(12) United States Patent
Chappo et al.

(10) Patent No.: US 7,477,721 B2
(45) Date of Patent: Jan. 13, 2009

(54) OPEN ACCESS AIR BEARING GANTRY

(75) Inventors: Marc A. Chappo, Elyria, OH (US); Leonard Plut, Mentor, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 71 days.

(21) Appl. No.: 11/568,227

(22) PCT Filed: Mar. 30, 2005

(86) PCT No.: PCT/IB2005/051070

§ 371 (c)(1),
(2), (4) Date: Oct. 24, 2006

(87) PCT Pub. No.: WO2005/102171

PCT Pub. Date: Nov. 3, 2005

(65) Prior Publication Data

US 2007/0230654 A1 Oct. 4, 2007

Related U.S. Application Data

(60) Provisional application No. 60/565,561, filed on Apr. 27, 2004.

(51) Int. Cl.
*G01N 23/083* (2006.01)
*H05G 1/02* (2006.01)
(52) U.S. Cl. .............................. 378/13; 378/19; 378/197
(58) Field of Classification Search ................ 378/13, 378/19, 197
See application file for complete search history.

(56) References Cited

U.S. PATENT DOCUMENTS

| | | | |
|---|---|---|---|
| 4,200,799 A * | 4/1980 | Saito ........................... 378/13 |
| 4,358,699 A | 11/1982 | Wilsdorf | |
| 4,415,635 A | 11/1983 | Wilsdorf et al. | |
| 4,723,259 A | 2/1988 | Amor et al. | |
| 4,799,245 A | 1/1989 | Bernardi | |
| 4,912,735 A * | 3/1990 | Beer ........................... 378/15 |
| 4,996,435 A * | 2/1991 | Keller ......................... 250/551 |
| 4,998,294 A | 3/1991 | Banks et al. | |
| 5,012,505 A * | 4/1991 | Zupancic et al. ............. 378/130 |
| 5,117,445 A | 5/1992 | Seppi et al. | |
| 5,134,639 A * | 7/1992 | Vekstein et al. ............... 378/15 |
| 5,185,675 A | 2/1993 | Banks | |
| 5,703,921 A | 12/1997 | Fujita et al. | |
| 5,784,428 A * | 7/1998 | Schmidt ........................ 378/4 |
| 6,245,440 B1 | 6/2001 | Kuhlmann-Wilsdorf et al. | |

(Continued)

FOREIGN PATENT DOCUMENTS

EP    1 016 375 A1    7/2000

*Primary Examiner*—Edward J Glick
*Assistant Examiner*—Thomas R Artman

(57) ABSTRACT

A diagnostic imaging system (10) includes an x-ray source (16), which is rotated around an examination region (20) on a rotating gantry (14). A subject, disposed on a couch (30), is translated longitudinally through the examination region (20). The imaging system is standardized such that a common subassembly is adapted to receive a bore (24) of any selectable diameter. The common subassembly includes a stationary gantry (12) and a bearing race (52) supported by bearing members (50). Standard motor modules (28), standard power slip ring modules (56), and standard information transmission modules (58) are disposed about the race (52). The number of the standard modules (28, 56, 58) is specified by a user.

14 Claims, 4 Drawing Sheets

U.S. PATENT DOCUMENTS

Figure 1:
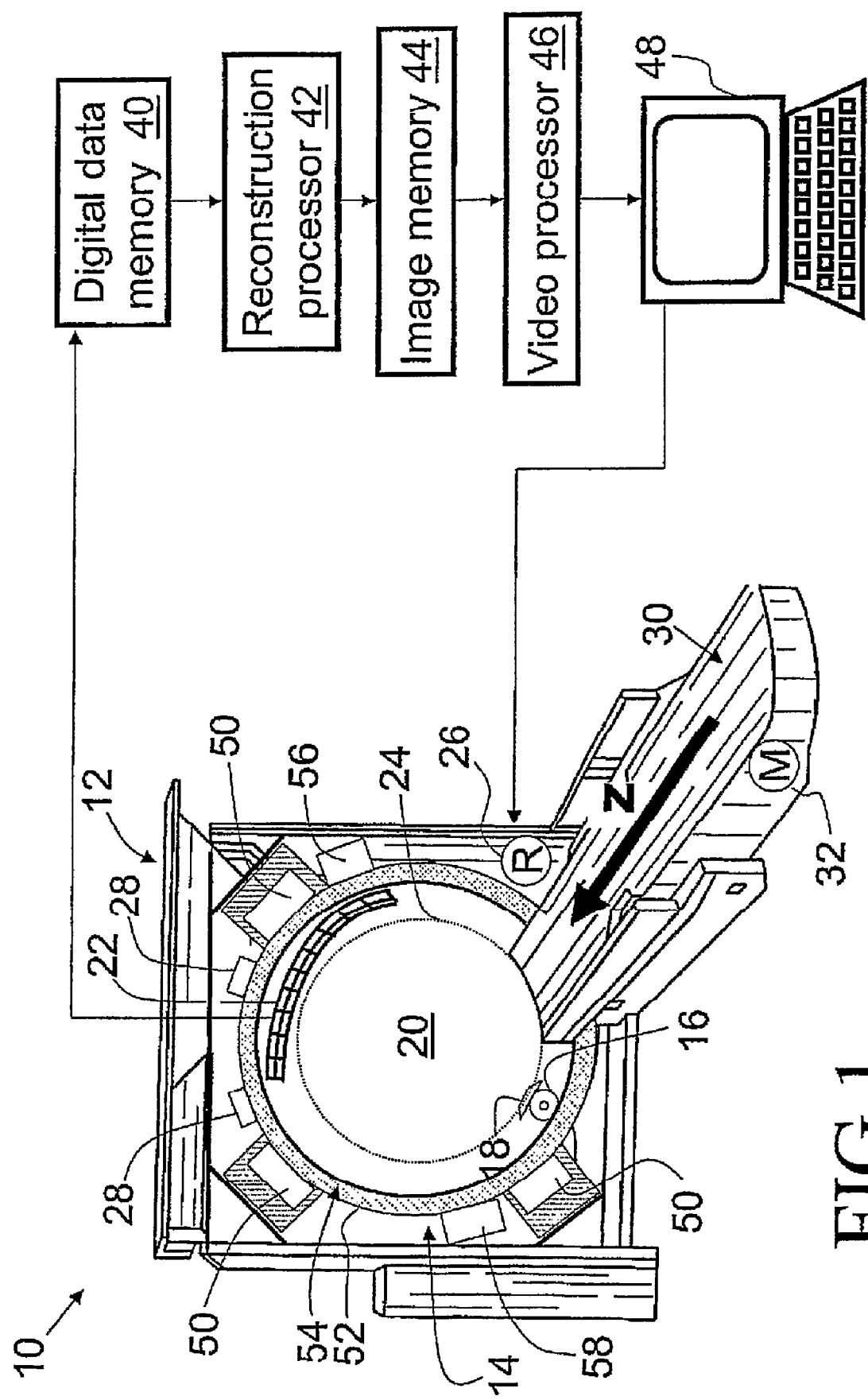

| | | | |
|---|---|---|---|
| 6,276,145 B1 * | 8/2001 | Sharpless et al. | 62/51.1 |
| 6,404,845 B1 | 6/2002 | Sharpless et al. | |
| 6,553,091 B2 | 4/2003 | Takanashi et al. | |
| 6,590,953 B2 * | 7/2003 | Suzuki et al. | 378/15 |
| 6,608,569 B2 * | 8/2003 | Herold et al. | 340/999 |
| 6,700,947 B2 * | 3/2004 | Oshima et al. | 378/15 |
| 6,718,005 B2 * | 4/2004 | Hamada et al. | 378/15 |
| 6,944,260 B2 * | 9/2005 | Hsieh et al. | 378/19 |
| 2002/0025023 A1 | 2/2002 | Herold et al. | |
| 2003/0035506 A1 | 2/2003 | Tybinkowski et al. | |
| 2003/0156678 A1 | 8/2003 | Hamada et al. | |
| 2004/0017895 A1 | 1/2004 | Suzuki et al. | |

* cited by examiner

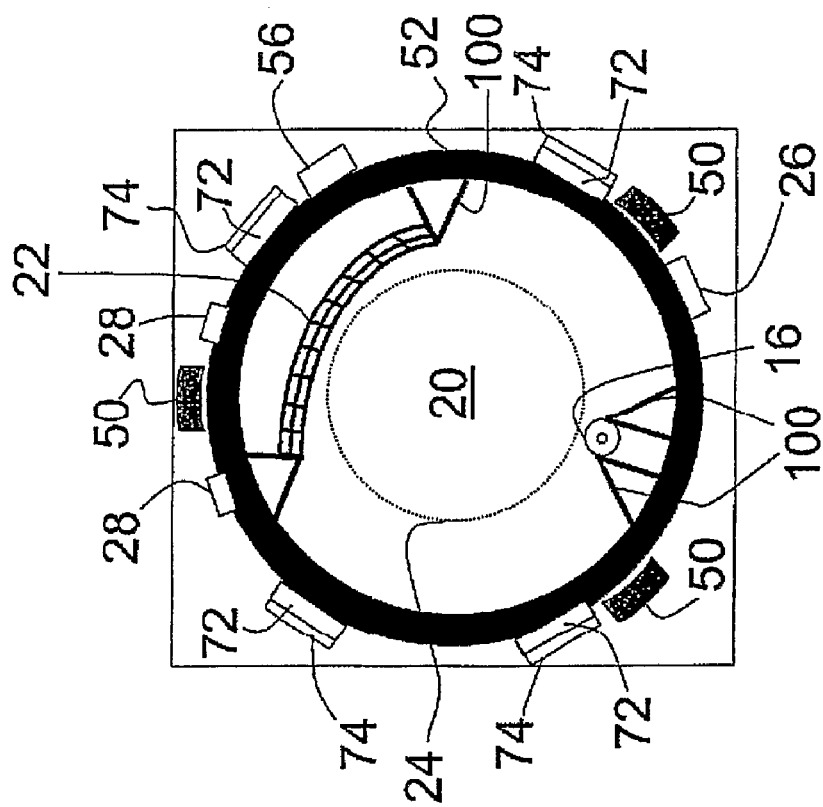
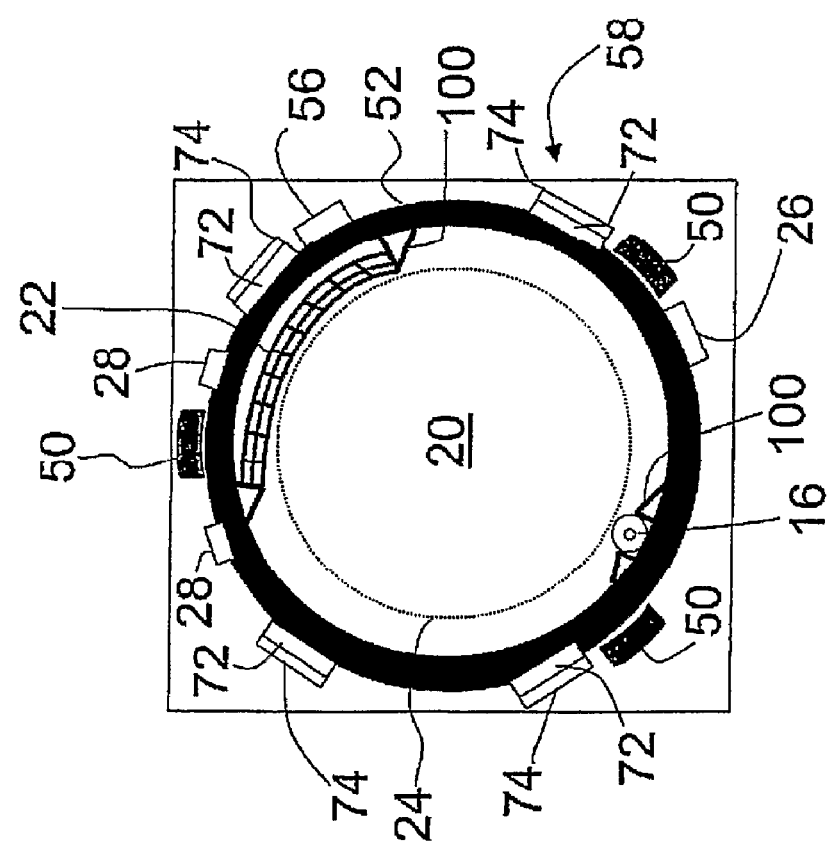
FIG 2A
FIG 2B

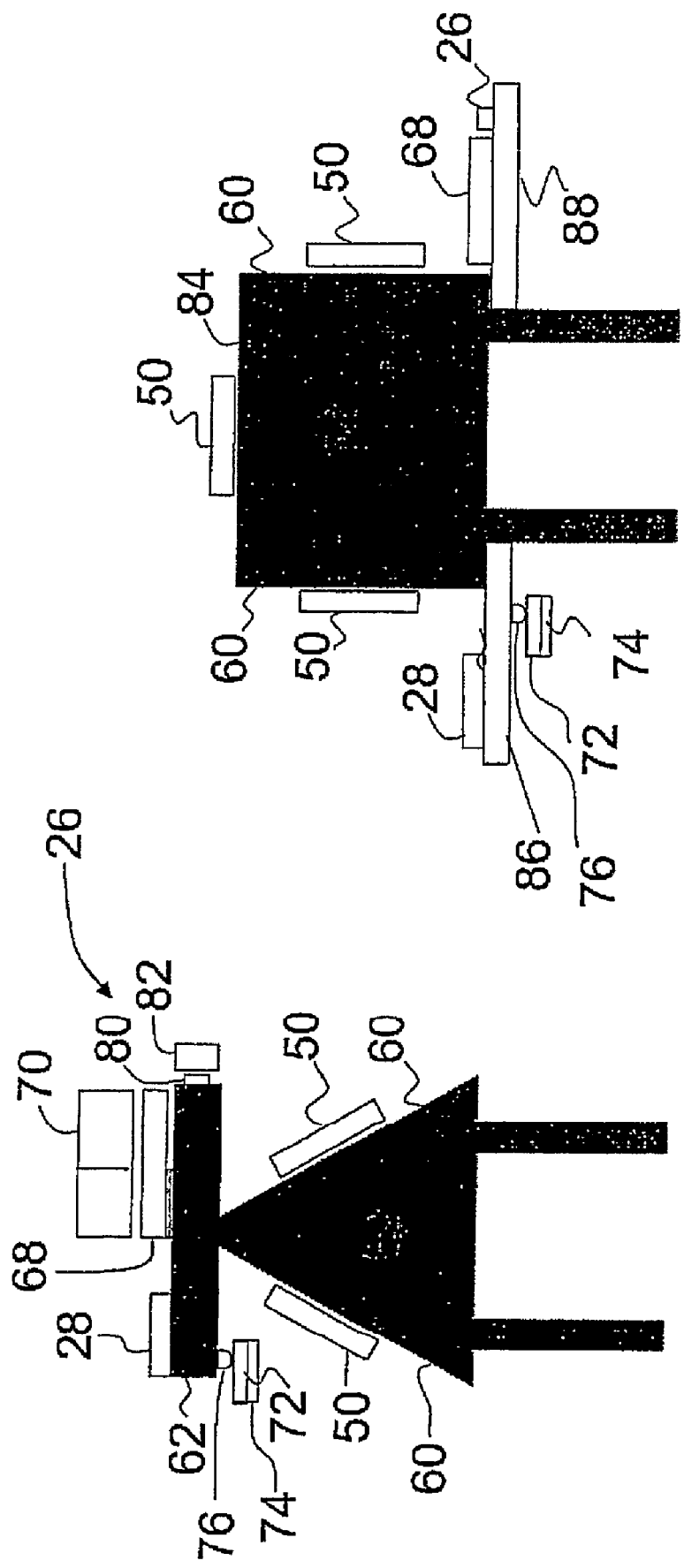

OPEN ACCESS AIR BEARING GANTRY

CROSS REFERENCE TO RELATED APPLICATIONS

This application claims the benefit of U.S. provisional application Ser. No. 60/565,561 filed Apr. 27, 2004, which is incorporated herein by reference.

DESCRIPTION

The present invention relates to the diagnostic imaging arts. It finds particular application in computed tomography, particularly with air bearing systems and will be described with particular reference thereto. However, the invention will also find application in other diagnostic imaging systems.

In computed tomography (CT) imaging, a subject is positioned on a subject table which moves the subject longitudinally through a bore of a CT scanner. An x-ray tube is mounted on a rotating gantry which rotates around the bore to project a fan beam, wedge beam, or cone beam of x-rays through an examination region defined by the bore. A one or two-dimensional radiation detector including an array of detector elements is mounted opposite to the x-ray tube to detect and measure intensities of radiation transmitted through the bore. A subject disposed in the examination region within the bore interacts with and absorbs a portion of the x-rays. Typically, the x-ray detector is also mounted on the rotating gantry. However, in some configurations, the x-ray detectors are mounted in a ring on a stationary gantry surrounding the rotating gantry. In either configuration, the intensity data from the x-ray detectors is reconstructed to produce a two or three-dimensional image representation of the portion of the subject in the imaging region in the bore.

For cost and technical considerations, typically, the gantry mechanical design is committed to minimizing the patient opening (bore diameter) which can accommodate the subject for which the CT scanner is designed. For a laboratory scanner, a 30 cm bore may be adequate. For many human examinations, a 40 or 50 cm bore is adequate. For oncology applications where auxiliary equipment accompanies the subject into the bore, an 80-90 cm bore is advantageous.

The rotating gantry is fit as close as possible to the bore. For example, the closer the x-ray tube is to the bore, the lower the centrifugal forces on the x-ray tube during rotation at a given speed. The rotating anode x-ray tubes used in CT scanners have tungsten anodes which can weigh about 2-4 kg. Operating an x-ray tube at higher centrifugal forces requires different bearings and other designs within the x-ray tube, i.e., higher centrifugal forces require more expensive x-ray tubes. Similarly when the x-ray detector rotates on the rotating gantry, the closer the x-ray detector is to the bore, the shorter circumferentially the x-ray detector becomes to span a given arc.

X-ray tubes use large amounts of electrical power, which must be communicated to the rotating gantry. This is typically done by a slip ring positioned as close as possible to the diameter of the bore. In current designs, the larger the diameter of the slip ring, the higher the cost. Moreover, the larger the diameter of the slip ring, the faster the speed between the slip ring and the brushes. The higher relative speeds require higher performance, hence more expensive brushes. Similar considerations apply to the mechanisms for conveying the data accumulated by the rotating detector from the rotating gantry back to the stationary portions of the gantry.

Further, the larger the diameter of the rotating gantry and the further out the heavy components are positioned, the greater its momentum when rotating at a given speed. Hence, as the diameter of the rotating gantry becomes larger, maintaining the same rate of acceleration correlates to increasingly more powerful motors. In order to reconstruct the data from the detector, the reconstruction processor needs an accurate measurement of the angular position of the x-ray source, hence the rotating gantry. To this end, current designs utilize precision encoders or other angular position measuring devices are typically mounted around the rotating gantry. Such angular position encoders or equivalent technology are typically very precise and the longer their circumferential length, the higher their cost becomes.

There are other advantages besides cost for minimizing the diameters of the rotating gantry and associated equipment. For example, as diameters or distances become larger, tolerances, the precision with which alignments have been made, and the like become more of an issue. Vibration can be more of an issue at larger diameters. Bearings and other hardware issues also become more complicated at larger diameters.

Accordingly, it is the common wisdom in the art that the rotating gantry of a CT scanner should be matched to the bore diameter and both have the smallest practical diameter. Although this tends to minimize the cost of the components for each scanner model, models with each bore diameter have a unique family of parts. Having unique parts for each scanner of a family of scanners with different diameters leads to the cost of custom design for each diameter scanner and a relatively large inventory of parts. This also results in unique point-designs which encumber high NRE costs and effectively lengthens time to market while reducing commonality of systems. These disadvantages of present art are exacerbated by faster rotational speeds and the ever-increasing number of simultaneous slices of detector image data which represent today's frontiers in CT scanner design.

The present invention contemplates a new and improved method and apparatus that overcomes the above-referenced problems and others.

In accordance with one aspect of the present invention, a CT scanner subassembly is disclosed. The subassembly includes a common stationary gantry frame and a radiation translucent bore of one of a plurality of selectable cross sectional sizes. A plurality of common bearing members is mounted to the stationary gantry. A common annular bearing race is rotatably supported on the bearing members. At least one common motor module rotates the annular bearing race. A means mounts an x-ray source and a radiation detector at any of a plurality of selectable distances radially inward from the bearing race such that the common bearing members and the bearing race are used to fabricate CT scanners with any of a plurality of bore sizes.

In accordance with another aspect of the present invention, a method of fabricating a CT scanner is disclosed. A common subassembly for the CT scanner is fabricated. A bore of an appropriate diameter is selected. The bore of the selected diameter is mounted to the common subassembly. An x-ray tube and an array of radiation detectors are mounted to the common subassembly.

One advantage of the present invention resides in providing a standard scanner subassembly for different patient apertures.

Another advantage resides in an easy performance upgrade by adding a larger number of the same modules.

Yet another advantage resides in reduced cost.

Still further advantages and benefits of the present invention will become apparent to those of ordinary skill in the art upon reading and understanding the following detailed

DESCRIPTION OF THE PREFERRED EMBODIMENTS

The invention may take form in various components and arrangements of components, and in various steps and arrangements of steps. The drawings are only for purposes of illustrating the preferred embodiments and are not to be construed as limiting the invention.

Figure 6:
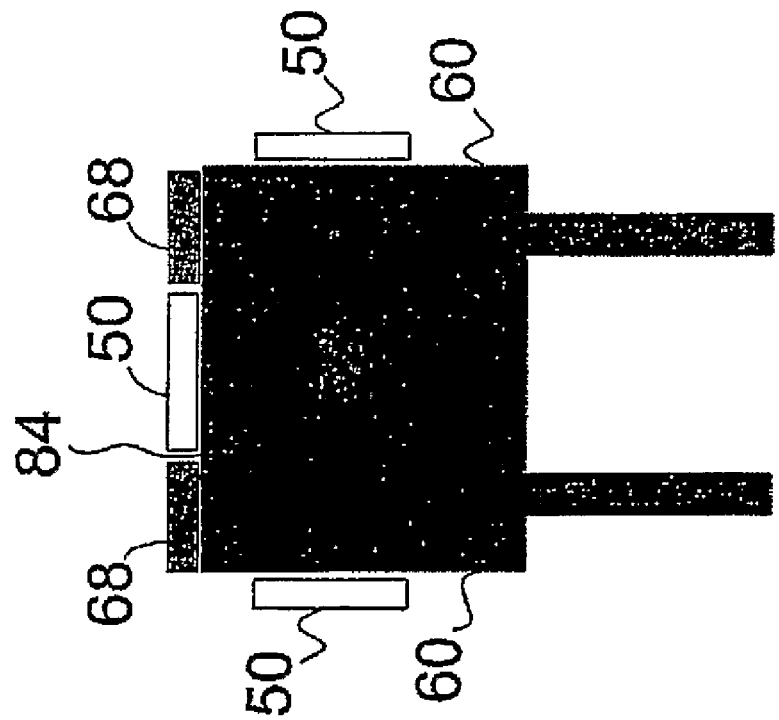
Figure 5:
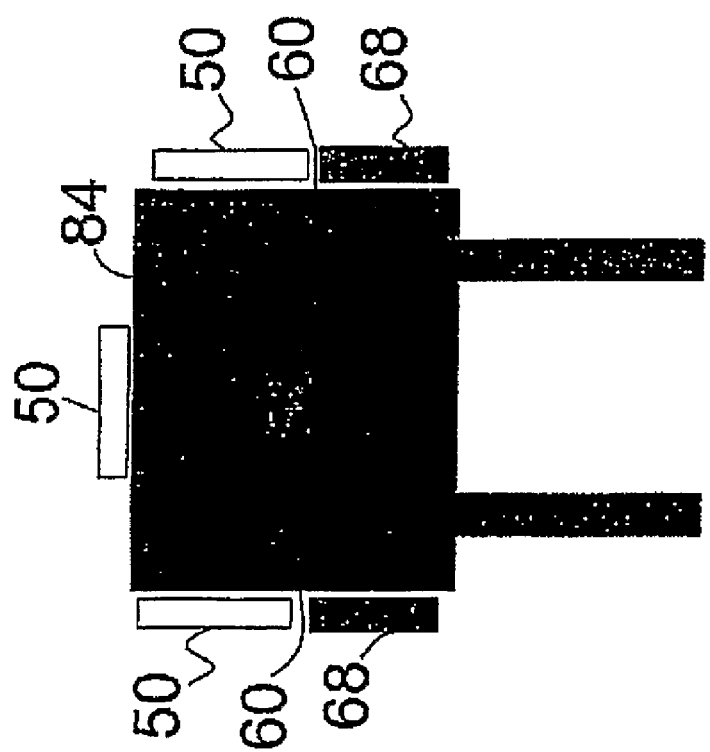

FIG. 1 shows an exemplary diagnostic imaging apparatus employing an air bearing system;

FIG. 2A schematically shows a scanner with a larger bore which;

FIG. 2B schematically shows a scanner with a smaller bore;

FIG. 3 is a cross sectional view which schematically shows mounting some of the imaging system components about a tapered air bearing race;

FIG. 4 schematically shows mounting some of the imaging system components about a rectangular air bearing race;

FIG. 5 schematically shows another mounting of some of the imaging system components about an air bearing race; and FIG. 6 schematically shows another mounting of some of the imaging system components about an air bearing race.

With reference to FIG. 1, a computed tomography (CT) imaging apparatus or scanner 10 includes a stationary gantry 12 that supports a rotating gantry 14. The stationary gantry 12 is sized to fit through the doorways or other portals into conventional imaging suites. An x-ray source such as x-ray tube 16 and a source collimator 18 cooperate to produce a fan-shaped, cone-shaped, wedge-shaped, or otherwise-shaped x-ray beam directed across an examination region 20 to an array of x-ray detectors 22. Preferably, the x-ray detectors 22 are mounted on the rotating gantry 14. The examination region 20 is defined within a cosmetic radiotranslucent bore or bezel 24 attached to the stationary gantry 12 to shield a subject from moving parts. A resolver or encoder 26 determines an angular orientation of the rotating gantry as it is rotated by one or more motors 28 on high speed bearings such as air bearings, magnetic bearings, or the like.

A subject support or patient couch 30 is driven by a motor 32 to move longitudinally along Z-axis into and through the examination region 20. Preferably, at least part of the patient couch is partially or completely radiotranslucent.

Projection data which are collected by the detector 22 are communicated to a digital data memory 40. A reconstruction processor 42 reconstructs the acquired projection data, using filtered backprojection, an n-PI reconstruction method, or other reconstruction method, to generate a three-dimensional image representation of the subject or of selected portion thereof which is stored in a volumetric image memory 44. The image representation is rendered or otherwise manipulated by a video processor 46 to produce a human-viewable image that is displayed on a graphical user interface 48 or another display device, printing device, or the like for viewing by an operator.

Preferably, the graphical user interface 48 is programmed to interface a human operator with the CT scanner 10 to allow the operator to initialize, execute, and control CT imaging sessions. The graphical user interface 48 is optionally interfaced with a communication network such as a hospital or clinic information network via which image reconstructions are transmitted to medical personnel, a patient information database is accessed, and the like.

With continuing reference to FIG. 1, the rotating gantry 14 is suspended from the stationary gantry 12 by a plurality of air bearing pads 50 as described in a great detail in U.S. Pat. No. 6,404,845 issued to Phillips Medical Systems. The air bearing pads 50 support an outer circumferential surface or air bearing race 52 of an aluminum rotor 54 of the rotating gantry 14 on a thin cushion of air to provide a nearly frictionless surface for the rotating gantry, thus making the bearing suitable for high speed rotation at reasonable system cost.

With reference to FIGS. 2A-2B, various common components, which are normally used in CT scanners, are mounted on the rotating gantry 14. As will be discussed in a greater detail below, the motor(s) 28, power slip ring and brush assemblies 56, encoder 26, information transmission assemblies 58, x-ray tube 16, detector 22 and other components are mounted in available areas of the air bearing system, adjacent or along the air bearing race 52. Placing the x-ray tube 16 and detector 22 near the rotor outer surface 52, as shown in FIG. 2A, defines a large bore scanner. Mounting the x-ray tube 16 and the detector 22 closer together, as shown in FIG. 2B, defines a smaller bore scanner. This has the advantage of standardizing CT scanner components and avoiding the need for a custom design for each bore size or specific application. Non-recurring engineering and recurring product costs are reduced through the use of common components. The use of common components affords compliance with ISO-14001 (environmental considerations) since common components require fewer consumables for production which is especially important for production of unique castings that is minimized.

With reference to FIG. 3, the air pads 50 are mounted on side periphery 60 of the air bearing race 52 which has a pair of converging bearing surfaces. In this embodiment, the same pads provide both radial and lateral support and guidance. The motor 28 is mounted about an outer ring 62 of the race 52. Preferably, the motor 28 is a linear induction motor (LIM) which is a segmented module spanning several degrees of arc. The motor 28 induces counter-acting magnetic fields in the race 52 which are used for propulsion. More motor modules 28 are added along the race 52 for CT scanner models in which the gantry is accelerated more rapidly. Optionally, the iron is added on or underlying the air bearing race surface that interacts with the linear motor 28 to improve efficiency. Optionally, magnets or windings of the linear motors 28 are embedded in the race 52. In this design, optionally, synchronous ring motors are preferably used.

With continuing reference to FIG. 3, the power slip ring and brush assembly 56 is mounted about the race 52. More specifically, a power slip ring or segment 68 is positioned about the outer ring 62 of the race 52. Although the power slip ring 68 can be a continuous concentric ring, it is preferably not a continuous ring but rather one or more segments 68 which span circumferentially around the race 52 such that at least one stationary power brush assembly 70 contacts each slip ring segment 68 at any given time. Generally, the more segments are used, the fewer brush holders per segment are needed to supply the electric power required. The opposite is also true, e.g. if the fewer number of segments is used, the more brush holders per segment are required. Each power brush assembly 70 includes a holder and a plurality of fiber wires (not shown) secured in the holder as described in U.S. Pat. No. 4,360,699 and U.S. Pat. No. 4,415,635 issued to the University of Virginia. The fiber wires contact the slip ring 68 via a radial mount. The fiber wire brushes enable the brush assembly 70 and the slip ring segment(s) 68 to move at any speed up to about 152.5 linear m/sec relative to each other. The fiber brush has a minimal wear, allowing the lifetime of hundreds millions of revolutions and virtual elimination of brush dust associated with carbon composite brushes utilized in many CT scanner slipring designs. The slip ring segment design provides more flexibility, ease of mounting and replacement and significant cost savings over present CT scanner slipring design. More like brush holders and/or like power slip segments are added for CT scanner models with higher power x-rays tubes, once again, in a modular, cost-effective fashion, without changing the gantry design.

Alternatively, rotating transformers can be used to transfer the electric power inductively. Optionally, the rotating portion of the transformer can be unified with the air bearing race.

With continuing reference to FIG. 3 and reference again to FIGS. 2A-2B, the information transmission assembly 58 is disposed about the race 52. Elliptical lenses 72 and light receivers or detectors 74 are stationary mounted along portions of the air bearing race 52 to receive light from a line of diodes 76 which are positioned around a peripheral surface. Each lens 72 extends over several degrees of arc and is designed to focus the light received at any point under the lens onto a common focal spot, e.g. the path to the focal point is constant and independent of the position of the rotating gantry 14. Preferably, the stationary gantry 12 is divided into quadrants with a single light-collecting assembly 72, 74 mounted in each. The light sources, i.e. light emitting diodes 76, are positioned on the rotating portion, such that at least one light emitting diode is optically connected to the light collecting assembly 72, 74 at any point in time. Four light collecting assemblies and a single circumferential line of light sources are sufficient to match at least the 5.3 gigabits/second data transfer rate of a current forty slice scanner. Of course, it is also contemplated that the collecting assemblies might be modularly added to increase the data transfer rate. In this case, the rotating gantry 14 is split into equal segments with the light sources currently in each quadrant operating in unison such that their lenses are equi-spaced around the air bearing race 52. Optionally, the data transfer rate is increased by utilizing sources with higher optical power output, and/or by using wave division multiplexing, and/or by electronically switching the light sources according to the quadrant the light sources are in, such that a contiguous channel is received by each light collecting assembly. In a similar manner, and with much less hardware and optical bandwidth, a bi-directional optical control link between the rotating portion of the gantry and its stator is implemented. This link can also be partially realized within the optical HW of the information transmission assembly.

With continuing reference to FIGS. 2A and 3, the resolver or encoder 26 is disposed about the outer ring 62 of the race 52. Preferably, the encoder 26 includes a plurality of tick marks or other regularly spaced timing elements 80 circumferentially spanning 360 degrees around the race 52. The tick marks 80 are etched in or otherwise attached to the race 52. An optical read head 82 reads the tick marks 80 as the rotating gantry 14 rotates and determines the angular position of the rotating gantry 14. Relatively new technology affords economical precision machining or etching of the tick marks, and the read head can perform very high speed reading of the absolute position tick marks on the bearing itself or on a separate assembly which is easily attached to the bearing, thus overcoming the cost/size issues on conventional resolvers and/or encoders. Magnetic ticks and magnetic read heads, optical encoder rings and like pick-ups, and the like are also contemplated.

With reference to FIG. 4, the air bearing race 52 has a rectangular cross-section. The air bearing pads 50 are mounted on the side periphery 60 and a radially outmost surface 84 of the race 52. Annular supports 86, 88 are extended from the race side periphery 60 to provide an annular mounting means or surface for the power slip rings 68, the encoder ring 26 and other appropriate components. The linear motors 28 can be coupled to one of the annular supports 86, 88 or can be interposed between the air bearings pads 50 to interact with the circumferential bearing surface or an underlying layer with more iron content.

With reference to FIGS. 5 and 6, the power slip rings 68 are mounted on the race side periphery 60 and the outmost surface 84. E.g., the power slip rings 68 might be mounted on the outer periphery of the rotor wherever space allows. Note that the position encoders and motors remain the same as shown in FIGS. 2A and 2B.

The invention has been described with reference to the preferred embodiments. Modifications and alterations will occur to others upon reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A CT scanner subassembly comprising:
   a common stationary gantry frame;
   a radiation translucent bore of one of a plurality of selectable cross sectional sizes attached to the common stationary gantry frame;
   a plurality of common bearing members mounted to the stationary gantry;
   a common annular bearing race rotatably supported on the bearing members;
   at least one common motor module for rotating the annular bearing race;
   a means for mounting an x-ray source and a radiation detector at any of a plurality of selectable distances radially inward from the bearing race such that the common bearing members and the bearing race are used to fabricate CT scanners with any of a plurality of bore sizes; and
   a rotor mounted to the annular bearing race, wherein the x-ray source and the radiation detector are mounted at first and second locations on the rotor to define a first size examination region and at third and fourth locations to define a second different size examination region.

2. The scanner as set forth in claim 1, wherein the race has one of a triangular and rectangular transverse cross-section.

3. The scanner as set forth in claim 1, wherein the at least one common motor module includes a linear induction motor module.

4. The scanner as set forth in claim 1, further including: plural motor modules to faster accelerate the bearing race.

5. The scanner as set forth in claim 1, wherein the at least one motor module is embedded in the race.

6. The scanner as set forth in claim 1, further including:
   a common power slip ring assembly disposed about the race, which supplies electric power at least to the at least one motor, which each slip ring assembly includes at least:
   an annular power slip ring section disposed at the race; and
   at least two brush holders mounted to the stationary frame.

7. The scanner as set forth in claim 6, further including: a plurality of fiber wire brushes secured in each holder.

8. The scanner as set forth in claim 6, further including: a plurality of the power slip ring assemblies.

9. The scanner as set forth in claim 1, further including: information transmission assemblies disposed about portions of the race to transmit and receive data, each information transmission assembly including:

plural emitters disposed on the race; and plural receivers disposed on the stationary frame.

10. The scanner as set forth in claim 9, further including:

at least one elliptical lens which receives light rays from the emitters and focuses the received light rays into a common focal point.

11. The scanner as set forth in claim 10, wherein the common bearing race is split into quadrants and further including:

one lens positioned in each associated quadrant such that when the bearing race rotates at least one light emitting diode is positioned under the one lens in each quadrant.

12. The scanner as set forth in claim 1, further including:

a plurality of timing elements disposed on the race; and a readout sensor disposed on the stationary gantry to read a position of the timing elements.

13. The scanner as set forth in claim 1, wherein the radiation translucent bore extends in a transverse direction with respect to a beam emitted by the x-ray source that illuminates the radiation detector so as to lie between the x-ray source and the radiation detector in the path of the beam, thereby providing a shield for a subject in the examination region from the x-ray source and the radiation detector.

14. An adaptable standardized modular imaging system including:

a standard stationary gantry frame;

a radiation translucent bore with one of a plurality of specified diameters attached to the standard stationary gantry frame;

a plurality of standard bearing members mounted to the stationary gantry;

a standard annular bearing race rotatably supported on the bearing members;

a rotor having an aperture, the rotor being coupled to the standard annular bearing race; wherein the radiation translucent bore-attaches to the standard gantry frame so as to lie partially within the aperture;

a variety of standard modules disposed on the rotor, each of the modules is modularly addable, which variety includes one or more of:

standard motor modules for rotating the annular bearing race, standard power slip ring modules for supplying electric power to rotating parts of the imaging system, and standard information transmission slip ring modules for transmitting data to the rotating parts of the imaging system and receiving the data therefrom; and a means for mounting an x-ray source and a radiation detector on the rotor at any of a plurality of selectable distances radially inward from the bearing race such that the standard bearing members and the standard bearing race are used to fabricate CT scanners with any of the plurality of bore diameters.

* * * * *